United States Patent
Ebinuma et al.

(10) Patent No.: US 7,781,171 B2
(45) Date of Patent: Aug. 24, 2010

(54) MEHOD OF PRETREATING SAMPLE AND IMMUNOLOGICAL ASSAY METHOD USING THE SAME

(75) Inventors: Hiroyuki Ebinuma, Ryugasaki (JP); Hirokazu Yago, Ryugasaki (JP); Yuka Akimoto, Ryugasaki (JP); Osamu Miyazaki, Ibaraki (JP); Takashi Kadowaki, Tokyo (JP); Toshimasa Yamauchi, Tokyo (JP)

(73) Assignees: Daiichi Pure Chemicals Co., Ltd., Tokyo (JP); Toudai TLO, Ltd., Tokyo (JP)

( * ) Notice: Subject to any disclaimer, the term of this patent is extended or adjusted under 35 U.S.C. 154(b) by 566 days.

(21) Appl. No.: 10/575,711

(22) PCT Filed: Oct. 15, 2004

(86) PCT No.: PCT/JP2004/015261

§ 371 (c)(1),
(2), (4) Date: Apr. 13, 2006

(87) PCT Pub. No.: WO2005/038458

PCT Pub. Date: Apr. 28, 2005

(65) Prior Publication Data

US 2007/0065891 A1    Mar. 22, 2007

(30) Foreign Application Priority Data

Oct. 15, 2003 (JP) .............................. 2003-354715

(51) Int. Cl.
*G01N 33/53* (2006.01)
(52) U.S. Cl. .......................... 435/7.1; 435/7.9; 436/518; 436/174
(58) Field of Classification Search ....................... None
See application file for complete search history.

(56) References Cited

U.S. PATENT DOCUMENTS

| | | | | |
|---|---|---|---|---|
| 4,086,059 A | * | 4/1978 | Willner et al. | 436/500 |
| 4,708,939 A | * | 11/1987 | Siedel et al. | 436/13 |
| 6,066,505 A | * | 5/2000 | Cheng et al. | 436/537 |

FOREIGN PATENT DOCUMENTS

| | | |
|---|---|---|
| JP | 8-509294 | 10/1996 |
| JP | 2656774 | 5/1997 |
| JP | 2000-304748 | 11/2000 |
| WO | 03/016906 | 2/2003 |

OTHER PUBLICATIONS

Tanaka, Sachiyo et al., "Outline of the Method for Measuring the Concentration of Blood Adiponectin", vol. 31, No. 8, pp. 763-766, 2003. (with partial English translation).

Hironori Waki, et al. "Impaired Multimerization of Human Adiponectin Mutants Associated With Diabetes", The Journal of Biological Chemistry, XP-002988190, vol. 276, No. 41, Oct. 10, 2003, pp. 40352-40362.

Tsu-Shuen Tsao, et al. "Role of Disulfide Bonds in ACRP30/Adiponectin Structure and Signaling Specificity", The Journal of Biological Chemistry, XP-002408187, vol. 278, No. 50, Sep. 30, 2003, pp. 50810-50817.

Yukio Arita, et al. "Paradoxical Decrease of an Adipose-Specific Protein, Adiponectin, in Obesity", Biochemical and Biophysical Research Communications, XP-000867719, vol. 257, No. 1, Apr. 1999, pp. 79-83.

Scherer, Philipp E. et al., "A Novel Serum Protein Similar to C1q, Produced Exclusively in Adipocytes", The Journal of Biological Chemistry, vol. 270, No. 45, pp. 26746-26749, 1995.

Hu, Erding et al., "AdipoQ Is a Novel Adipose-specific Gene Dysregulated in Obesity", The Journal of Biological Chemistry, vol. 271, No. 18, pp. 10697-10703, 1996.

Maeda, Kazuhisa et al., cDNA Cloning and Expression of a Novel Adipose Specific Collagen-like Factor, apM1 (Adipose Most Abundant Gene Transcript 1), Biochemical and Biophysical Research Communications, vol. 221, No. 2, pp. 286-289, 1996.

Nakano, Yasuko et al., "Isolation and Characterization of GBP28, a Novel Gelatin-Binding Protein Purified from Human Plasma", J. Biochem., vol. 120, No. 4, pp. 803-812, 1996.

Ouchi, Noriyuki et al., "Adiponectin, an Adipocyte-Derived Plasma Protein, Inhibits Endothelial NF-kB Signaling Through a cAMP-Dependent Pathway", Circulation, vol. 102, pp. 1296-1301, 2000.

Yamauchi, T. et al, "The fat-derived hormone adiponectin reverses insulin resistance associated with both lipoatrophy and obesity", Nature Medicine, vol. 7, No. 8, pp. 941-946, 2001.

Santini, Helene, "Rebirth of the health-care system in Cambodia", The Lancet Supplement, vol. 360, pp. 57-58, 2002.

Pajvani, Utpal B. et al., "Structure-Function Studies of the Adipocyte-secreted Hormone Acrp30/Adiponectin", The Journal of Biological Chemistry, vol. 278, No. 11, pp. 9073-9085, 2003.

Fruebis, Joachim et al., "Proteolytic cleavage product of 30-kDa adipocyte Complement-related protein increases fatty acid oxidation in muscle and causes weight loss in mice", Proc. Natil. Acad. Sci., vol. 98, No. 4, pp. 2005-2010, 2001.

U.S. Appl. No. 10/575,931, filed Apr. 14, 2006, Ebinuma, et al.

* cited by examiner

*Primary Examiner*—Patricia A Duffy
(74) *Attorney, Agent, or Firm*—Oblon, Spivak, McClelland, Maier & Neustadt, L.L.P.

(57) ABSTRACT

The invention provides a method of pretreating a sample for conveniently, quickly and accurately measuring the total amount of adiponectin present in a biological sample contaminated with various adiponectin multimers.

The method of measuring an sample for immunologically assaying the total amount of adiponectin present in the sample comprises reacting, with an adiponectin-containing sample, at least one of a reducing agent, an acid or a salt thereof, a surfactant, and a protease.

14 Claims, 2 Drawing Sheets

MEHOD OF PRETREATING SAMPLE AND IMMUNOLOGICAL ASSAY METHOD USING THE SAME

TECHNICAL FIELD

The present invention relates to a method of pretreating a sample for conveniently, quickly and accurately assaying the total amount of adiponectin present in the sample, and to an immunological method of assaying the total amount of adiponectin using said pretreatment.

BACKGROUND ART

Adiponectin (see Non-Patent Documents 1 to 4) is a secretion-type protein expressed specifically and abundantly in white adipose tissue. Adiponectin is a plasma protein (about 30 kDa) belonging to the C1q family and is composed of 244 amino acids.

Adiponectin possesses a trimeric structure of triple helix, in which each monomer is formed of an N-terminal collagen-like domain with multiple Gly-X-Y repeats and a C-terminal globular domain. Also, it has been reported that, in blood, a plurality of trimers are linked to one another to form higher order products (hereinafter may be referred to as "various multimers").

In recent years, adiponectin has been reported to exist in human blood at a high level of 5 to 10 μg/mL, and exerts a variety of physiological activities. In particular, adiponectin suppresses growth of smooth muscle cells and prevents monocytes from adhering onto endothelial cells. From these findings, adiponectin is considered to have anti-arteriosclerosis effect (Non-Patent Document 5). Moreover, from the findings that when adiponectin is administered to a mouse suffering from type 2 diabetes or lipoatrophic diabetes, insulin resistance is reversed and hyper-FFA (free fatty acid) in blood and hyper-TG (triglyceride) in blood are alleviated, adiponectin is reported to function as an insulin-sensitive hormone and to exhibit ameliorating effect on diabetes (Non-Patent Document 6). It is also reported that renal failure patients who show low blood adiponectin levels have a high risk of complications of cardiovascular diseases and show low survival rates, and that, in a study performed on native Americans of the Pima tribe who are known to develop insulin resistance and type 2 diabetes at a high incidence, onset of type 2 diabetes is suppressed among subjects showing high blood adiponectin (Non-Patent Document 7).

The above findings suggest the possibility that adiponectin might be an endocrine factor responsible for linking the excessive accumulation of visceral fat directly with onset of insulin resistance. Therefore, blood adiponectin level is considered a predictive factor for the onset of diabetes or arteriosclerosis, and measurements of such levels are expected to serve as a useful indicator of lifestyle-related diseases.

According to a method for determining the total amount of various multimers of adiponectin contained in a blood sample, a sample is boiled in the presence of sodium dodecylsulfate (SDS) to expose antibody-recognizing sites of various multimers which have been hidden stereostructually, and then immunoassay is performed (Patent Document 1). However, this method has some problems in that it requires an apparatus for boiling treatment (100° C.) and it is also actually difficult to make itself available to automation of two steps; i.e., boiling treatment and subsequent immunoassay.

A kit called "HUMAN ADIPONECTIN RIA KIT" (Cat. #HADP-61HK) is commercially available (LINCO RESEARCH, INC.). However, given that the kit utilizes the two-antibodies/PEG method, in which $^{125}$I-labelled mouse adiponectin and human adiponectin are competed and anti-adiponectin polyclonal antibody is used for capture, it should be noted that handling of this kit is cumbersome, and in addition, there remain concerns about safety, specificity, and quality of the reagents. In order to make it possible that the specificity in the above method established on the basis of the competitive reaction continues to be constant, there is need for the conditions under which the reactivity of anti-adiponectin polyclonal antibody against the $^{125}$I-labelled mouse adiponectin and various human adiponectin multimers continue to be constant. However, as described before, a biological sample contains various multimers in a mixed state, and the proportions of the respective multimers vary. Thus, this kit essentially involves the problem that total adiponectin cannot be measured accurately.

In addition, there is a prior art document disclosing a monoclonal antibody which recognizes non-denatured adiponectin having a specific stereostructure that has not been modified by any denaturation treatment with, for example, SDS or heat (see Patent Document 2, the adiponectin of this type is referred to as native adiponectin in this reference), and an assay method utilizing the monoclonal antibody (Patent Document 2). However, this method has the problem that total adiponectin of a biological sample cannot be measured accurately as it contains various multimers at varying proportions because the form of adiponectin present in a sample (for example, the number of trimers and trimer aggregation condition) affects reactivity of adiponectin with the above-mentioned monoclonal antibody.

The structural form of adiponectin has been investigated with respect to a recombinant, though not in a biological sample. According to such investigation, when adiponectin is treated with dithiothreitol (DTT) at low pH (Non-Patent Document 8) or with trypsin (Non-Patent Document 9), the structural form thereof changes. However, there is no information about results of an immunoassay of the adiponectin subjected to such a treatment.

As described above, in order to immunologically determine the total adiponectin level of a sample, the sample must be subjected to a pretreatment process to thereby attain a uniform reactivity between each of the multimer species (a trimer and various multimers composed of trimers) and the antibody employed. However, there has been no convenient method whose two steps; i.e., the pretreatment step and the immunoassay step, can be automated.

[Patent Document 1] Japanese Patent Application Laid-Open (kokai) No. 2000-304748

[Patent Document 2] PCT International Publication WO03/016906

[Non-Patent Document 1] Scherer P. E., et al., J. Biol. Chem. 270, 26746-26749, 1995

[Non-Patent Document 2] Hu E., et al., J. Biol. Chem. 271, 10697-10703, 1996

[Non-Patent Document 3] Maeda K., et al., Biochem. Biophys. Res. Commun. 221, 286-289, 1996

[Non-Patent Document 4] Nakano Y., et al., J. Biochem. 120, 803-812, 1996

[Non-Patent Document 5] Ouchi N, et al., Circulation, 102, 1296-1301, 2000

[Non-Patent Document 6] Yamauchi T, et al., Nature Med. 7, 941-946, 2001

[Non-Patent Document 7] Lindsay R. S., et al., Lancet, 360, 57-58, 2002

[Non-Patent Document 8] Utpal B. Pajvani, et al., J. Biol. Chem. 278, 9073-9085, 2003

[Non-Patent Document 9] Fruebis, J., et al., Proc. Natil. Acad. Sci. 98, 2005-2010, 2001

DISCLOSURE OF THE INVENTION

Problems to be Solved by the Invention

An object of the present invention is to provide a method of pretraeting a sample for conveniently, quickly and accurately assaying the total amount of adiponectin in a biological sample which contains trimers and various multimer species composed of trimers. Another object of the invention is to provide an immunoassay method for determining the total amount of adiponectin by making use of such a pretreatment method.

Means for Solving the Problems

The present inventors have made extensive research with the aim of solving the above-mentioned problems, and have found that when trimers and various multimers composed of trimers are treated with at least one of a reducing agent, an acid or a salt thereof, a surfactant, and a protease, and then analyzed by means of polyacrylamide gel electrophoresis (polyacrylamide: 2-15%; hereinafter referred to as PAGE (2-15%)), stained bands attributable to various multimers that had existed before the treatment disappeared or reduced their intensities, and that, an adiponectin-derived converted product (hereinafter referred to as a converted product) is detected at a position corresponding to a lower molecular weight as compared to the positions corresponding to any other bands that existed before the treatment. The inventors have also confirmed that the converted product has reactivity with an anti-adiponectin antibody, and that the converted product can be measured by use of the anti-adiponectin antibody.

On the basis of the above findings, the present inventors have further conducted research, and have found that when a sample is treated with a pretreatment agent containing at least one of a reducing agent, an acid or a salt thereof, a surfactant, and a protease, and then immunoassay of the sample is performed, total adiponectin level of a biological sample containing various multimers can be determined without boiling the sample together with the pretreatment agent, leading to completion of the invention.

Accordingly, the present invention provides a method of pretreating an adiponectin measurement sample for immunologically assaying the total amount of adiponectin in the sample, characterized by adding, to an adiponectin-containing sample, at least one of a reducing agent, an acid or a salt thereof, a surfactant, and a protease, and allowing the same to react with the sample without boiling together with the sample.

The present invention also provides a pretreatment agent required for pretreating a sample for immunologically assaying the total amount of adiponectin in the sample, wherein the pretreatment agent contains at least one of a reducing agent, an acid or a salt thereof, a surfactant, and a protease; and, in use, the pretreatment agent is allowed to react with the sample without undergoing boiling together with the sample.

The present invention also provides a method for determining the total amount of adiponectin in a sample, characterized by adding, to an adiponectin-containing sample, at least one of a reducing agent, an acid or a salt thereof, a surfactant, and a protease, allowing the same to react with the sample without boiling together with the sample, and performing an immunological assay of adiponectin.

The present invention further provides an immunoassay reagent for assaying the total amount of adiponectin in a sample, characterized by the reagent including a first reagent and a second reagent, the first reagent containing at least one of a reducing agent, an acid or a salt thereof, a surfactant, and a protease, and the second reagent containing an insoluble carrier carrying an antibody for determining adiponectin level, wherein the sample is allowed to react with the first reagent while boiling is not performed.

Effect of the Invention

According to the present invention, the total amount of adiponectin in a biological sample in which various multimer species are present in a mixed state can be determined conveniently, quickly, and accurately.

BEST MODE FOR CARRYING OUT THE INVENTION

Figure 1:
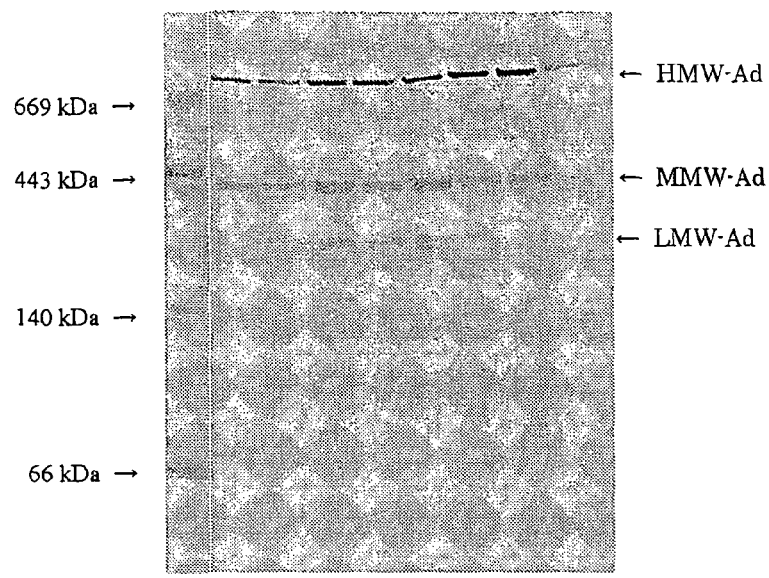
[FIG. 1]Results of western blotting of human serum adiponectin.

As described above, in a biological sample, adiponectin exist in the form of various multimers, and the proportions of respective multimers are not always the same. Therefore, when immunoassay is performed, it is postulated that reactivity between the antibody to be employed in measurement and each species of the various multimers differs from species to species. Specifically, particular multimers may become difficult to be assayed. Moreover, if a hypothetical situation is considered in which a sandwich assay system is performed on a sample containing one molecule of a hexamer and one molecule of a trimer—which means that there exist 9 monomers in the sample—from interpretation of the assay results, this case may not be distinguished from, for example, the case where there are two molecules of a trimer or the case where there are two molecules of a hexamer. In either case, assay results do not correctly reflect total adiponectin. Incidentally, a method employing a pretreatment of degrading multimers by boiling the sample in the presence of SDS will provide assay results that correctly reflect total adiponectin; however, the pretreatment in this method is cumbersome and, in addition, difficulty is encountered for automating the two steps of pretreatment and the subsequent immunoassay.

On the basis of the above-mentioned findings, the present inventors have conceived that the problem can be solved when the immunological assay is performed after various multimers have been converted, while not undergoing boiling, to a certain specific form that attains a uniform reactivity between the antibody used in the assay and the various multimers contained in the sample and thus provides assay results which correctly reflect total adiponectin.

As a pretreatment method that meets the above purpose for an assay of various adiponectin species contained in a sample, at least one member selected from among a reducing agent, an acid or a salt thereof, a surfactant, and a protease is added to a sample containing adiponectin, and the one or more selected members are allowed to react with adiponectin without boiling of the sample. The converted products obtained from any of these pretreatment methods may have the same property or different properties from method to method. Here, the various multimers may be composed of monomers alone, trimers alone, or specific multimers. Further, the converted products obtained from the pretreatment may have molecular weights falling within a certain molecular weight range. In other words, any pretreatment method will be useful so long as the converted products have such a property and configuration that ensure binding of an antibody selected for establishing an immunoassay system thereto at certain reactivity.

No particular limitation is imposed on the biological sample to be employed in the present invention, so long as the biological sample contains various multimers of adiponectin such as body fluids (e.g., blood and urine), tissue extracts, and culture supernatants of tissue-derived cells obtained from a mammal such as human, monkey, goat, sheep, rabbit, mouse, rat, guinea pig etc. . . . Of these, blood (serum, plasma) is preferred, because it provides information related to diabetes or arteriosclerosis and thus has become of interest these days. No particular limitation is imposed on the method for obtaining a sample, so long as the method does not affect adiponectin present in the sample in terms of the purpose of performing the total adiponectin assay.

No particular limitation is imposed on the reducing agent which may be used in the pretreatment method, the pretreatment agent, the immunoassay, or the immunoassay reagent of the present invention, so long as the reducing agent exhibits reducing power capable of breaking the disulfide linkage of adiponectin and provides substantially no effect on the immunoassay. For example, mention may be given of thiol compounds such as DTT (dithiothreitol), 2-mercaptoethanol, cysteamine, and thioglycerol; borohydride compounds; and phosphines. The concentration at which the reagent is used is appropriately determined so that a converted product of interest may be obtained. For example, when a thiol compound is used, DTT or 2-mercaptoethanol is preferably used. The treatment with a reducing agent is preferably performed at 4 to 60° C. for 5 to 24 hours.

No particular limitation is imposed on the acid or a salt thereof, and any organic acid or inorganic acid may be employed so long as it can break the linkage between various multimers of adiponectin. For example, there may be employed acetic acid, citric acid, hydrochloric acid, formic acid, tartaric acid, and oxalic acid. The concentration at which the acid or a salt thereof is used is appropriately selected so that a converted product of interest may be obtained. Preferably, the concentration ranges from 1 to 1000 mM, more preferably 10 to 200 mM. The acid or a salt thereof may also be used as a buffer, and in such a case, pH of the buffer is preferably 4 or less. The treatment with the acid or a salt thereof is preferably performed at 4 to 60° C. for 5 to 24 hours.

No particular limitation is imposed on the choice of the surfactant, and ionic, nonionic, and other types of surfactants may be employed so long as the surfactant can act on a variety of multimers, can transform different forms of adiponectin into such a form that enables measurement of the total amount of adiponectin for immunoassay, and can maintain reactivity between adiponectin and an adiponectin-specific antibody. In particular, anionic surfactants are preferred, and specifically, alkyl sulfates such as dodecyl sulfate and alkylbenzene sulfonates such as dodecylbenzene sulfonates are more preferred. These surfactants may be used singly or in combination. The concentration at which such a surfactant is used generally ranges from 0.01 to 10%, but the range of 0.1 to 5% is more preferred. When the surfactant is used in combination with a treatment with an acid or a salt thereof, even more preferred effects will be obtained.

No particular limitation is imposed on the protease so long as it can act on a variety of multimers, and can transform different forms of adiponectin into such a form that enables measurement of total adiponectin in an immunoassay. The concentration at which the protease is used may be appropriately determined so that a converted product of interest may be obtained. No particular limitation is imposed on the origin of protease, and there may be employed any protease species derived from microorganisms, animals, and plants. Preferably, protease species derived from microorganisms, such as those belonging to genus Bacillus, genus Streptomyces, or genus Aspergillus. Examples of commercially available Bacillus-derived proteases include Protease type X (Sigma Co.); Protin AC, Protin PC (these two are both products of Daiwa Kasei); Protease S "Amano" (Amano Enzyme Co.); and Sumizyme CP (Shin Nihon Chemical Co., Ltd.). Examples of commercially available Streptomyces-derived proteases include Protease type XIV (Sigma), Pronase (Rosche), and Actinase AS (Kaken Seiyaku). Examples of commercially available Aspergillus-derived proteases include Protease A "Amano," Protease P "Amano," and Umamizyme (these are all products of Amano Enzyme); and Sumizyme MP (Shin Nihon Chemical Co., Ltd.). These proteases may be those obtained through the gene recombination technology, and may have undergone chemical modification. The treatment conditions under which a biological sample is treated with protease differ depending on the identity of the protease employed. Preferably, the treatment is performed in a phosphate buffer, Tris buffer, Good's buffer, or a similar buffer at 4 to 60° C. for 5 to 24 hours. The concentration of protease employed in the treatment is determined in consideration of reaction temperature, reaction time, etc., and generally ranges from 0.01 to 100 mg/ml.

No particular limitation is imposed on the manner in which respective items of the above-mentioned reducing agent, acid or a salt thereof, surfactant, and protease are used. They may be used singly or in combinations. For example, the following process may be performed: a reducing agent or an acid is allowed to react with a sample containing adiponectin, and subsequently, the reaction mixture is treated with protease. Moreover, during use of these items of reducing agents, acids and salts thereof, surfactants, and protease, additional components may also be added for purposes of regulating the environment in which the above items act on adiponectin or improving storage stability of the mentioned items. Examples of such additional components include buffer components such as phosphate buffer, glycine buffer, Tris buffer, and Good's buffer; surfactants which do not act on various multimers; bovine serum albumin (BSA); sucrose; preservatives (such as sodium azide); and salt concentration regulators (such as sodium chloride).

No particular limitation is imposed on the choice of the antibody to be employed in the immunoassay of the present invention, so long as total adiponectin can be measured after at least one member selected from among a reducing agent, an acid or a salt thereof, a surfactant, and a protease is allowed to react with various adiponectin multimers without any boiling treatment. Of such antibody species, a polyclonal antibody includes a plurality of antibodies capable of specifically binding to a plurality of epitopes present on adiponectin transformed into a certain structural form. The polyclonal antibody can be obtained through immunizing an appropriate animal species (such as rabbit, goat, sheep, horse, cow, mouse, and rat) with adiponectin through a known method. Meanwhile, a monoclonal antibody may be one or more different monoclonal antibodies capable of specifically binding to an adiponectin transformed into a certain structural form. Such monoclonal antibodies may be prepared through an appropriate method, or a combination of known methods in the cell fusion technology, to thereby establish fusion cell lines capable of producing monoclonal antibodies, and through use of such cell lines. Moreover, polyclonal antibodies and monoclonal antibodies capable of specifically binding to adiponectin that has been transformed into a certain structural form may be available on the market and used in the present invention. Depending on the structural form of adiponectin, the following antibodies, for example, may be employed: Goat α human Acrp30 antibody (Cosmo Bio Co., Ltd., GT Co.), Rabbit α hu adiponectin-PoAb (Cosmo Bio Co., Chemicon Co.), hu Acrp30-MoAb (Fujisawa Pharmaceutical Co., Ltd., BD Co.), Mouse α hu Adiponectin MoAb (Cosmo Bio Co., Chemicon Co.), Anti-human ACRP30 monoclonal antibody (AX773, AX741, Ne, Na, Wako Pure Chemical Industries, Ltd.), etc.

As the antigen to be used for obtaining an antibody employed in the present invention, there may be used adiponectin that has been purified and isolated from a sample through a known method. There may alternatively be used adiponectin that has undergone treatment, but not boiling treatment, with a pretreatment solution containing at least one member selected from among a reducing agent, an acid or a salt thereof, a surfactant, and a protease. The antigen may be prepared in the form of a recombinant protein through use of conventional genetic engineering technology on the basis of the nucleotide sequence information of the protein.

The immunoassay of the present invention is based on a method which includes the following process: allowing an antibody capable of specifically binding to adiponectin that has been transformed into a certain structural form to be bonded to an insoluble carrier, to thereby capture the transformed adiponectin, whereby the presence or absence of adiponectin in the sample is determined (qualitatively) or the adiponectin level is determined quantitatively. Specific examples of the immunoassay include LTIA (latex turbidimetric immunoassay), ELISA (enzyme immunoassay), CLEIA (chemiluminescent enzyme immunoassay), RIA (radioimmunoassay), etc. Of these, LTIA is a method in which an insoluble carrier carrying an antibody capable of binding to adiponectin that has been transformed into a certain structural form is mixed with adiponectin that has been transformed into a certain structural form, to induce cross-linking (aggregation) of the insoluble carrier by the mediation of the transformed adiponectin, and thereby the turbidity that results is optically determined. According to this method, the presence or absence of adiponectin can be determined (qualitatively), or the adiponectin level can be determined quantitatively. This method is beneficial as it provides a simple, rapid, and accurate measurement of adiponectin.

The insoluble carrier to be employed in the present invention may be an organic insoluble carrier which has been employed in conventional immunoassay reagents and which can be produced industrially on a large scale. In LTIA, polystyrene latex particles are preferred, as they exhibit excellent antibody adsorption and maintain biological activity stably for a long period of time. In ELISA, a 96-well microplate made of, for example, polystyrene is preferred.

Various methods have been known for binding an antibody to such an insoluble carrier, and any of such known methods may be employed in the present invention as desired. For example, an antibody may be bound (sensitized) through physical adsorption to the surface of an insoluble carrier. Alternatively, the surface of an insoluble carrier having a functional group may be efficiently sensitized with an antibody through a known physical or chemical binding method.

No particular limitation is imposed on the reaction conditions under which the reaction of an antibody-carrying insoluble carrier and adiponectin that has been transformed into a certain structural form occurs, so long as antigen-antibody reaction occurs under the reaction conditions. No particular limitation is imposed on the reaction mixture, so long as the reaction mixture allows antigen-antibody reaction to proceed with the adiponectin that has undergone pretreatment to have a certain structural form. For example, the reaction mixture may contain a buffer component for adjusting pH (e.g., phosphate buffer, glycine buffer, Tris buffer, Good's buffer); a surfactant, sodium chloride, or a similar substance for preventing non-specific reactions; a stabilizer such as bovine serum albumin (BSA); and sucrose, polysaccharide polymers or a similar substance. The reaction mixture may also contain, in addition to the above substances which control the reactivity, water-soluble polysaccharide such as dextran; a neutralizer for neutralizing the reducing agent or acid contained in the aforementioned treatment agent; or an inactivating agent for protease, according to needs.

Exemplary detection methods performed in the above-mentioned LTIA or ELISA include the method described below. No particular limitation is imposed on the method for determining the degree of aggregation of insoluble carrier in LTIA. For example, in order to qualitatively or semi-quantitatively evaluate aggregation, the degree of aggregation may be determined visually through comparison in turbidity between samples having known concentrations and the target sample. In order to quantitatively evaluate aggregation, preferably, optical measurement is employed, from the viewpoint of convenience and accuracy. The optical measurement of aggregation may be performed through a known method. Specific examples of the optical measurement which may be employed in the present invention include so-called turbidimetric measurement (formation of aggregated mass is observed as an increase in turbidity), particle size distribution measurement (formation of aggregated mass is observed as a change in particle size distribution or in mean particle size), and integrating sphere turbidimetric assay (change in forward scattered radiation caused by formation of aggregated mass is measured with an integrating sphere, and the ratio in intensity to transmitted radiation is compared). When ELISA is performed, no particular limitation is imposed on the method for assaying a reaction product between a substrate and an enzyme, on the basis of enzyme activity of the enzyme-labeled antibody. Specifically, the wavelength intrinsic to the enzyme reaction product; for example, absorbance at 492 nm, may be read with a 96-well microplate reader.

EXAMPLES

The present invention will next be described in detail by way of examples, which should not be construed as limiting the invention thereto.

The reagents and materials employed in the Examples and Test Examples are as follows.

<Reagents and Materials> a. solution for washing antibody-binding resin (hereinafter referred to as wash solution): 0.1M $NaHCO_3$—NaOH (pH 8.3) containing 0.5M NaCl;

b. solution for eluting antibody-binding resin (hereinafter referred to as eluting solution): 0.1M Glycine-HCl (pH 2.5);

c. solution for neutralizing antibody-binding resin (hereinafter referred to as neutralizing solution): 2M Tris-HCl (pH 8.0);

d. latex: polystyrene particles latex (mean particle size: 0.2 μm, solid content: 10% (w/v), product of SEKISUI CHEMICAL CO., LTD.);

e. antibody carrying latex preparation buffer: 20 mM Tris-HCl (pH 8.0);

f. blocking buffer: 20 mM Tris-HCl (pH 8.0) containing 2% BSA;

g. LTIA buffer (R1): 20 mM Tris-HCl (pH 8.0) containing 0.15% BSA and 0.15M NaCl;

h. ELISA plate: 96-well microplate (product of NUNC);

i. ELISA antibody sensitization solution: PBS (pH 7.4);

j. ELISA buffer: PBS (pH 7.4) containing 1% BSA and 0.1% Tween 20;

k. Goat α human Acrp30 antibody: product of Cosmo Bio Co., Ltd., GT, Cat No. 421065 (commercial product of anti-human adiponectin polyclonal antibody);

l. hu Acrp30-MoAb: product of Fujisawa Pharmaceutical Co., Ltd., BD Transduction Laboratories, product code: A12820 (commercial product of anti-human adiponectin monoclonal antibody);

m. Goat α rabbit IgG HRP-labeled antibody: Cosmo Bio Co., Ltd., product of Capple;
n. ELISA wash solution: PBS (pH 7.4) containing 0.05% Tween 20; and
o. ELISA buffer 2: PBS (pH 7.4) containing 1% BSA and 0.05% Tween 20.

Referential Example 1

Preparation of *E. coli* Recombinant Mouse Globular Adiponectin (rMgAd)

A globular domain sequence (corresponding to residues 104-247) of the mouse adiponectin gene sequence (NCBI accession #U37222) was inserted between BamHI and HindIII of a 6×His-tag-containing pQE30 vector, and then introduced into *E. coli*. Recombinant mouse globular adiponectin (rMgAd) expressed in *E. coli* was purified through the following process. Specifically, a soluble fraction of *E. coli* was applied to Ni-NTA agarose (product of QIAGEN), and rMgAd was allowed to bind thereto for 16 hours at 4° C., followed by serial elution with imidazole. The fraction containing adiponectin was collected and then dialyzed with PBS for three days. The protein content of the resultant rMgAd was determined by means of a Bio-Rad DC protein assay kit.

Referential Example 2

Preparation of Anti-rMgAd Antibody rMgAd (50 μg) obtained in Referential Example 1 above and the same amount of Freund's complete adjuvant were mixed together, and two rabbits were immunized with the mixture six times, at two-week intervals, to produce antiserum. Specific antibody (IgG) present in the antiserum was purified through a conventional method by use of Protein A resin (anti-rMgAd antibody).

Referential Example 3

Purification of Adiponectin (mAd) Derived from Human Blood

The anti-rMgAd antibody (500 mg) prepared in Referential Example 2 above was bound to CNBr-activated Sepharose 4B (Amersham Bioscience) (50 mL), to thereby prepare anti-rMgAd antibody-binding Sepharose 4B resin. Human serum (2.5 L) was added to the anti-rMgAd antibody-binding Sepharose 4B resin, and the resin was washed thoroughly with the wash solution. The eluting solution was used to elute a human serum adiponectin (mAd) fraction, and the neutralizing solution was added to the eluted fraction in a volume 1/10 that of the fraction, to effect neutralization. Thereafter, the neutralized fraction was added to Protein A resin, and the fraction containing components which are not adsorbed to the Protein A resin was collected as purified mAd. The adiponectin content was determined by means of a "human adiponectin ELISA kit" (Otsuka Pharmaceutical Co., Ltd.).

Referential Example 4

Production of Anti-Human Adiponectin Monoclonal Antibody

The purified mAd (20 μg) obtained in Referential Example 3 above was mixed with the same amount of Freund's complete adjuvant, and two mice were immunized with the mixture three or four times, at two-week intervals. The mixture was again administered to the mice three days before cell fusion. Spleen cells were collected from the immunized mice, and cell fusion was performed with P3U1 myeloma cells through a conventional method using polyethylene glycol. Fused cells which produce anti-human adiponectin monoclonal antibody were selected through a known method. Specifically, wells that were highly reactive with mAd were selected through ELISA, and limiting dilution was performed. The selected fused cells were intraperitoneally administered to mice which had been treated with pristane, and the ascites was collected as anti-human adiponectin monoclonal antibody. Purification of the specific antibody (IgG) from the ascites was performed through a conventional method by use of Protein A resin. Thus, fused cells that produce eleven anti-human adiponectin monoclonal antibodies as well as such monoclonal antibodies (identification numbers 64401 to 64411) were obtained.

Referential Example 5

Preparation of Antibody Sensitizing Latex

A latex solution (1 volume) and an antibody carrying latex preparation buffer (4 volumes) were mixed, to thereby prepare a diluted latex solution. Each of an anti-rMgAd antibody and an anti-human adiponectin monoclonal antibody (64401) was diluted to 1 mg/mL with the preparation buffer, to thereby prepare a diluted antibody solution. Each (1 volume) of the resultant two diluted antibody solutions was added to and mixed with the above-prepared diluted latex solution (1 volume) under stirring. After a further stirring of the resultant mixture, blocking buffer (2 volumes) was added thereto, followed by stirring. Thus, there were obtained an anti-rMgAd-carried latex stock solution and a anti-human adiponectin monoclonal antibody-carried latex stock solution (64401).

Test Example 1

Analysis of Adiponectin Multimer in Human Serum through Western Blotting

Each (0.2 μL) of serum samples obtained from eight healthy subjects was subjected to PAGE (2 to 15%). The isolated material was transferred onto a PVDF membrane through semi-dry blotting. The membrane was subjected to immunostaining. The procedure of immunostaining is as follows. The material-transferred membrane was subjected to blocking with PBS solution (pH 7.4) containing 5% skim milk and 0.1% NaN$_3$. The resultant membrane was washed with PBS solution (pH 7.4) containing 0.1% Tween 20, and the thus-washed membrane was allowed to react with a commercially available anti-human adiponectin monoclonal antibody (hu Acrp30-MoAb; product of Fujisawa Pharmaceutical Co., Ltd., BD Transduction Laboratories) (1 μg/mL) at room temperature for 1 hour. Subsequently, the thus-reacted membrane was washed thoroughly with PBS solution (pH 7.4) containing 0.1% Tween 20. Through use of Vector ABC kit (Mouse) and a DAB substrate kit (FUNAKOSI), color was developed. As a result, three main bands were detected as stained, indicating that various multimers of adiponectin present in blood were mainly classified into three types (FIG. 1). As identified in electrophoresis profiles of FIG. 1, types of adiponectin corresponding to these three stained bands were named "HMW-Ad," "MMW-Ad," and "LMW-Ad" fractions from the top (high molecular weight) toward the bottom.

Example 1

Processing of Purified mAd Through a Reducing Agent, Acid or Salt thereof, or Protease The purified mAd obtained in Referential Example 3 was treated through use of a reducing agent, an acid or salts thereof, or a protease, singly or in combination. In each case, the treated purified mAd was observed for any change in form.

1) Processing Through a Reducing Agent or an Acid

Several buffers (50 mM each) such as Tris-HCl buffer (pH 8.5) and sodium acetate buffers (pH 3.0 and pH 4.0) were prepared so as to contain purified mAd. Under the presence or absence of a reducing agent (10 mM DTT), the samples were heated at 37° C. for 60 minutes. The thus-treated mixtures were subjected to PAGE (2 to 15%), followed by protein staining through use of CBB. A stained image of a sample containing Tris-HCl (pH 8.5) without DTT (processing condition 1) was employed as a control, and increase or decrease in intensity of bands corresponding to HMW-Ad, MMW-Ad, and LMW-Ad fractions under the respective processing conditions was observed. In addition, production of bands attributed to new converted products was observed (Table 1).

As a result, under the conditions where the reducing agent was not added and the pH values of the sodium acetate buffer were 3.0 and 4.0 (processing conditions 3 and 5), the stained band corresponding to the HMW-Ad fraction disappeared and intensity of the stained band corresponding to the MMW-Ad fraction increased. Meanwhile, under the conditions where the reducing agent was added and the pH values of the sodium acetate buffer were 3.0 and 4.0 (processing conditions 4 and 6), the stained bands corresponding to HMW-Ad, MMW-Ad, and LMW-Ad fractions disappeared and a new stained band attributed to a converted product derived from each fraction was observed. Under processing condition 2 (Tris-HCl, pH 8.5), a new band attributed to a converted product derived from each fraction was observed, but a band attributed to an HMW-Ad fraction did not completely disappear.

From the results described above, when multimeric adiponectin (HMW-Ad, MMW-Ad, and LMW-Ad) was treated with a reducing agent, an acid, or a salt thereof, it was confirmed that a new converted product was produced from the multimeric adiponectin. The thus-produced converted product was assumed to be an adiponectin trimer.

2) Processing with Protease

Purified mAd and a commercially available protease were added to 50 mM phosphate buffer (pH 8.0), followed by heating at 37° C. for 60 minutes. The thus-treated mixture was subjected to PAGE (2 to 15%), followed by protein staining with CBB. A stained image of Tris-HCl (pH 8.5) containing no DTT (processing condition 1) was employed as a control, and increase or decrease in intensity of bands corresponding to HMW-Ad, MMW-Ad, and LMW-Ad fractions under each of the processing conditions was observed. In addition, production of new bands attributed to converted products was observed (Table 2).

Through processing under any of processing conditions 7 to 9, all the stained bands corresponding to HMW-Ad, MMW-Ad, and LMW-Ad fractions disappeared and a new stained band attributed to converted products derived from these fractions was observed in a low molecular weight region. Through processing under any of conditions 10 to 12, stained bands corresponding to LMW-Ad and MMW-Ad fractions disappeared and new bands attributed to converted products derived from these fractions were observed in low molecular weight regions. In this case, no change was observed for the stained bands attributed to an HMW-Ad fraction.

From the results described above, when multimeric adiponectin (HMW-Ad, MMW-Ad, and LMW-Ad) was treated with protease, a new converted product was confirmed to be produced from the multimeric adiponectin. The positions at which the bands of these converted products were detected by PAGE (2 to 15%) ranges from 30 to 42 kDa, though the positions were somewhat shifted depending on the type of the protease employed.

In addition, the proteases employed in processing conditions 10 to 12 were found to be able to convert all the fractions to new products through a procedure including pretreatment of multimeric adiponectin with an acid or a salt thereof to convert the HMW-Ad fraction to the MMW-Ad fraction, followed by treatment with respective proteases.

TABLE 1

| | Processing condition | | | | | |
|---|---|---|---|---|---|---|
| | 1 | 2 | 3 | 4 | 5 | 6 |
| Buffer | Tris-HCl | Tris-HCl | acetic acid —NaOH | acetic acid —NaOH | acetic acid —NaOH | acetic acid —NaOH |
| pH | 8.5 | 8.5 | 3.0 | 3.0 | 4.0 | 4.0 |
| reducing agent | — | added | — | added | — | added |
| Adiponectin multimer | | | | | | |
| HMW-Ad | ++ | + | − | − | − | − |
| MMW-Ad | ++ | − | +++ | − | +++ | − |
| LMW-Ad | ++ | − | ++ | − | ++ | − |
| Converted product | − | +++ | − | +++ | − | +++ |

(+): Decrease,
(++): Unchanged,
(+++): Increase, or production of converted product
(−): Disappeared, or no production of converted product

TABLE 2

|  | Processing condition | | | | | |
| --- | --- | --- | --- | --- | --- | --- |
|  | 7 | 8 | 9 | 10 | 11 | 12 |
| Protease | Protease type XIV | Protease type X | Protin AC | Protease P "Amano" | Protease A "Amano" | Umamizyme |
| Adiponectin multimer |  |  |  |  |  |  |
| HMW-Ad | − | − | − | ++ | ++ | ++ |
| MMW-Ad | − | − | − | − | − | − |
| LMW-Ad | − | − | − | − | − | − |
| Converted product | +++ | +++ | +++ | +++ | +++ | +++ |

(+): Decrease,
(++): Unchanged,
(+++): Increase, or production of converted product
(−): Disappeared, or no production of converted product Example 2

Reactivity of Latex Reagent with Adiponectin Species

Figure 2:
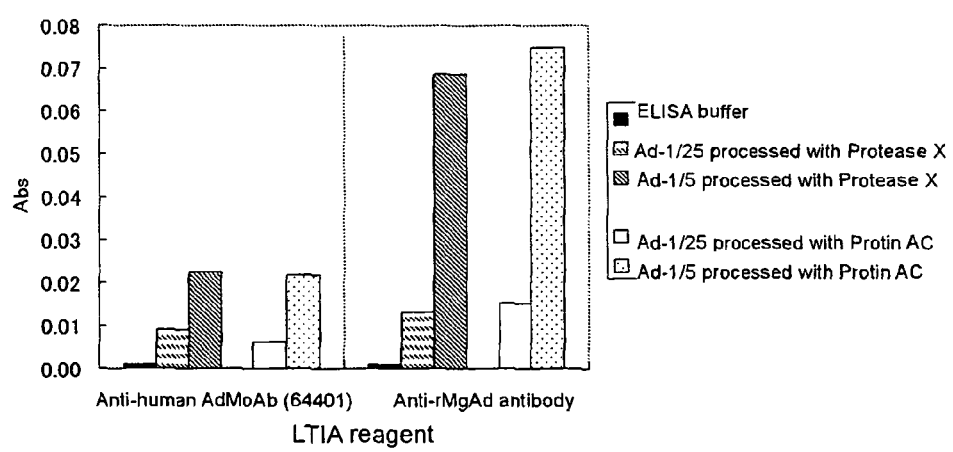
[FIG. 2]Charts showing reactivity between an LTIA reagent and protease-treated adiponectin.

The protease-treated purified mAd was diluted with ELISA buffer to obtain 5-fold and 25-fold diluted samples. Each of the latex stock solutions prepared in Referential Example 5 was diluted 10-fold with antibody carrying latex preparation buffer, and the resultant diluted solution was employed as Reagent 2. Samples (10 µL) were analyzed using Reagent 1 (LTIA buffer (R1))(100 µL) and Reagent 2 (100 µL) with Hitachi 7170 automatic biochemistry analyzer (Hitachi, Ltd.) under the following conditions: wave length: 570 nm; measurement points: 18 to 34. The results are shown in FIG. 2.

For both cases of the anti-rMgAd antibody latex reagent and anti-human adiponectin monoclonal antibody (64401) latex reagent, absorbance varies in accordance with the concentration of the Protin AC- or Protease Type X-treated human serum adiponectin.

Accordingly, Protin AC and Protease Type X were found to be able to convert adiponectin multimers to new products retaining antibody recognizing sites which can be recognized by anti-rMgAd antibody and the anti-human adiponectin monoclonal antibody (64401). Thus, it has been confirmed that these proteases can be used in pretreatment for measurement of total adiponectin in a biological sample.

Example 3

Reactivity of ELISA Reagent with Adiponectin Species

Figure 3:
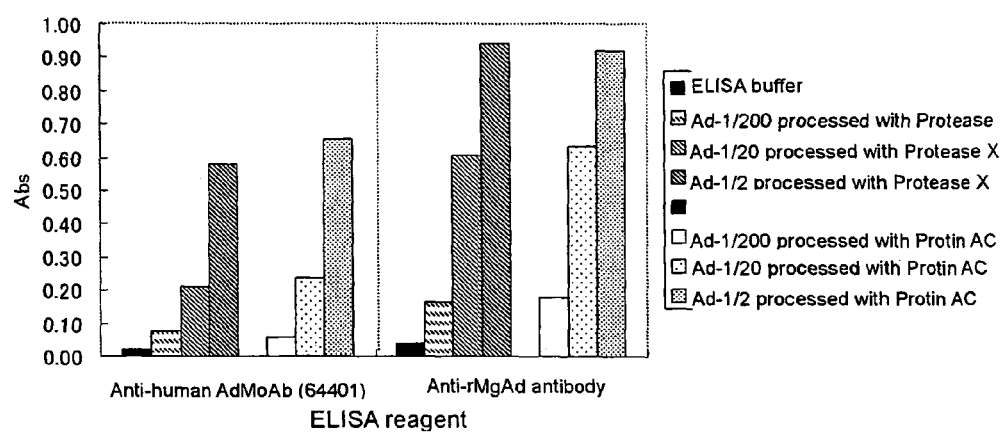
[FIG. 3]Charts showing reactivity between an ELISA reagent and protease-treated adiponectin.

A Goat α human Acrp30 antibody and an anti-human adiponectin monoclonal antibody (64401) was each diluted to 1 µg/mL with an ELISA antibody sensitization solution. Subsequently, an ELISA plate was sensitized with the resultant mixture, followed by blocking with an ELISA buffer. The protease-treated mAd was diluted with the ELISA buffer to obtain 2-fold, 20-fold, and 200-fold diluted samples. The thus-obtained samples were reacted in the ELISA plate at room temperature for 1 hour. The plate was washed with the ELISA buffer, and then reacted at room temperature for 1 hour with an anti-rMgAd antibody solution which had been diluted 10,000-fold with the ELISA buffer. Subsequently, the plate was washed with the ELISA buffer, and then reacted at room temperature for 1 hour with a Goat α rabbit IgG HRP-labeled antibody solution which had been diluted 1,000-fold with the ELISA buffer. The plate was washed with the ELISA buffer, and color was allowed to develop through HRP enzymatic reaction with tetramethylbenzidine and hydrogen peroxide. 2N Sulfuric acid was added to the reaction mixture. Absorbance at 450 nm was measured. The results of measurement are shown in FIG. 3.

When a combination of anti-human adiponectin monoclonal antibody (64401) and the anti-rMgAd antibody, or a combination of Goat α human Acrp30 antibody and the anti-rMgAd antibody is used for ELISA, absorbance varies in accordance with the concentration of the Protin AC- or Protease Type X-treated human serum adiponectin.

Accordingly, Protin AC and Protease Type X were found to be able to convert adiponectin multimers to new products retaining antibody recognizing sites which can be recognized by Goat α human Acrp30 antibody, anti-human adiponectin monoclonal antibody (64401), and anti-rMgAd antibody. Thus, it has been confirmed that these proteases can be used in pretreatment for measurement of total adiponectin in a biological sample.

Test Example 2

Analysis of Adiponectin Multimers Derived from Human Blood

Figure 4:
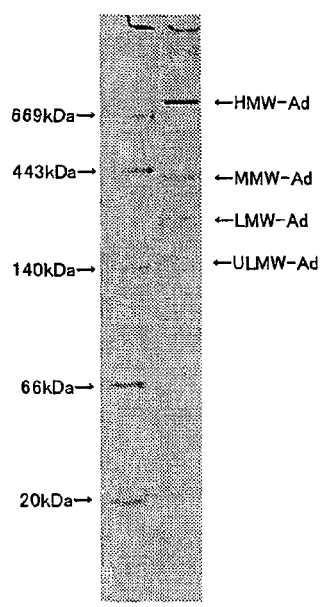
[FIG. 4]Electrophoresis profiles obtained by CBB-staining of human-serum-derived purified adiponectin separated through PAGE (2-15%) in Referential Example 3.

Purified mAd was freshly prepared in accordance with Referential Example 3, and was subjected to PAGE (2 to 15%), followed by protein staining with Coomassie Briliant Blue (CBB) (FIG. 4). Subsequently, the product was subjected to immunostaining with a commercially available anti-human adiponectin monoclonal antibody (hu Acrp30-MoAb) in a manner similar to that employed in Test Example 1, and the stained image was analyzed. The results indicated that adiponectin multimer purified from human serum had at least four types of adiponectin, consisting of three types observed in Test Example 1 and one type detected in a small amount in this Test Example. As identified in electrophoresis profiles of FIG. 1, types of adiponectin corresponding to these four CBB-stained bands were named "HMW-Ad," "MMW-Ad," "LMW-Ad," and "ULMW-Ad" fractions from the top (high molecular weight) toward the bottom.

Example 4

Processing of Purified mAd Through a Reducing Agent, Acid or a Salt thereof, a Surfactant, or Protease The purified mAd analyzed in Test Example 2 was treated through use of a reducing agent, an acid or a salt thereof, a surfactant, or a protease, singly or in combination. The thus-treated purified mAd was observed for any change in structural form.

1) Combination of a Reducing Agent and an Acid

Several buffers (100 mM each) such as Tris-HCl buffer (pH 8.5) and sodium citrate buffers (pH 3.0 to pH 6.0) were prepared so as to contain purified mAd. Under the presence or absence of a reducing agent (10 mM 2-mercaptoethanol), those buffers were heated at 37° C. for 30 minutes. The thus-treated mixtures were subjected to PAGE (2 to 15%), followed by protein staining through use of CBB. A stained image of a sample containing Tris-HCl (pH 8.5) without 2-mercaptoethanol (processing condition 13) was employed as a control, and increase or decrease in intensity of bands corresponding to HMW-Ad, MMW-Ad, LMW-Ad, and ULMW-Ad fractions under the respective processing conditions were observed. In addition, production of bands attributed to new converted products was observed (Table 3).

As a result, when no reducing agent was added and the pH of the sodium citrate buffer was 4.0 or higher (processing conditions 15, 17, and 19), as the sodium citrate buffer acidifies, stained bands corresponding to an HMW-Ad fraction tended to disappear, and instead, intensity of bands of an MMW-Ad fraction increased. Under processing condition 21 (pH 3.0), a new stained band attributed to a converted product which migrated a distance longer than ULMW-Ad was observed. Meanwhile, under conditions 14 and 16, where a reducing agent was added and pH was 6.0 or higher, stained bands attributed to HMW-Ad remained to be present, whereas under processing conditions 18 and 20 (pH 5.0 and 4.0), stained bands corresponding to all the fractions disappeared, and in addition, a new broad stained band was observed at a position almost the same as that of ULMW-Ad. Under processing condition 22 (pH 3.0), a new broad band attributed to converted products was observed at a position almost the same as that observed under processing condition 21.

From the results described above, when multimeric adiponectin (HMW-Ad, MMW-Ad, LMW-Ad, and ULMW-Ad) was treated with a reducing agent and an acid or a salt thereof, a new converted product was confirmed to be produced. In addition, it was surmised that the converted products produced in processing condition 21 were adiponectin dimers, the converted products produced in processing conditions including addition of a reducing agent (processing conditions 14, 16, 18, and 20) were adiponectin trimers, and the converted products produced in processing condition 22 was adiponectin monomers. The stained bands were extracted, and analyzed to confirm that ULMW-Ad was an adiponectin trimer and LMW-Ad was an adiponectin trimer bound by albumin.

TABLE 3

| | Processing condition | | | | | | | | | |
|---|---|---|---|---|---|---|---|---|---|---|
| | 13 | 14 | 15 | 16 | 17 | 18 | 19 | 20 | 21 | 22 |
| Buffer | Tris-HCl | | citric acid-NaOH | | citric acid-NaOH | | citric acid-NaOH | | citric acid-NaOH | |
| pH | 8.5 | | 6.0 | | 5.0 | | 4.0 | | 3.0 | |
| reducing agent | | added | | added | | added | | added | | added |
| Adiponectin multimer | | | | | | | | | | |
| HMW-Ad | ++ | + | ++ | + | + | − | − | − | − | − |
| MMW-Ad | ++ | − | ++ | − | +++ | − | +++ | − | − | − |
| LMW-Ad | ++ | − | ++ | − | ++ | − | ++ | − | − | − |
| ULMW-Ad | ++ | − | ++ | − | ++ | − | ++ | − | − | − |
| Converted product | − | +++ | − | +++ | − | +++ | +++ | +++ | +++ | +++ |

(+): Decrease,
(++): Unchanged,
(+++): Increase, or production of converted product
(−): Disappeared, or no production of converted product 2) Processing with Protease Purified mAd and a commercially available protease were added to 50 mM phosphate buffer (pH 8.0) (to the final concentration of 1 mg/ml for each), and the resultant mixture was heated at 37° C. for 60 minutes. The thus-treated mixture was subjected to PAGE (2 to 15%), followed by protein staining through use of CBB. Subsequently, a stained image of Tris-HCl (pH 8.5) containing no DTT (processing condition 1) was employed as a control, and increase or decrease in intensity of bands corresponding to HMW-Ad, MMW-Ad, LMW-Ad, and ULMW-Ad fractions under respective processing conditions was observed. In addition, production of new bands attributed to converted products was observed (Table 4).

Under any of processing conditions 23 to 25, all the stained bands corresponding to HMW-Ad, MMW-Ad, LMW-Ad, and ULMW-Ad fractions disappeared and a new stained band attributed to converted products derived from these fractions was observed in a low molecular weight region. Through processing under any of processing conditions 26 to 28, stained bands corresponding to ULMW-Ad, LMW-Ad, and MMW-Ad fractions disappeared and new bands attributed to converted products derived from these fractions were observed in low molecular weight regions. In this case, no change was observed for the stained bands attributed to an HMW-Ad fraction.

From the results described above, when multimeric adiponectin (HMW-Ad, MMW-Ad, LMW-Ad, and ULMW-Ad) was treated with protease, a new converted product was confirmed to be produced from the multimeric adiponectin. The positions at which the bands of these converted products were detected by PAGE (2 to 15%) ranges from 30 to 42 kDa, though the positions were somewhat shifted depending on the type of the protease employed. The stained bands were extracted, and subjected to amino acid analysis, which revealed that these converted products were globular adiponectin.

In addition, the proteases employed under processing conditions 26 to 28 were found to be able to convert all the fractions to new products through a procedure including pretreatment of multimeric adiponectin with an acid or a salt thereof to convert the HMW-Ad fraction to the MMW-Ad fraction, followed by treatment with respective proteases.

TABLE 4

|  | Processing condition | | | | | |
| --- | --- | --- | --- | --- | --- | --- |
|  | 23 | 24 | 25 | 26 | 27 | 28 |
| Protease | Protease type XIV | Protease type X | Protin AC | Protease P "Amano" | Protease N "Amano" | Proteinase K |
| Adiponectin multimer | | | | | | |
| HMW-Ad | – | – | – | ++ | ++ | ++ |
| MMW-Ad | – | – | – | – | – | – |
| LMW-Ad | – | – | – | – | – | – |
| ULMW-Ad | – | – | – | – | – | – |
| Converted product | +++ | +++ | +++ | +++ | +++ | +++ |

(+): Decrease,
(++): Unchanged,
(+++): Increase, or production of converted product
(–): Disappeared, or no production of converted product Example 5

Measurement of Total Blood Adiponectin Through Processing with Acid and Surfactant in Combination (1) Preparation of Pretreatment Solution A commercially available surfactant was added to a 100 mM sodium citrate buffer (pH 3.0, used for establishing an acid treatment). The surfactants employed are SDS and Neoperex F65 (product of KAO CORPORATION), which are anionic surfactants; Cortamine 24P and Cortamine 86P (product of KAO CORPORATION), which are cationic surfactants; and Triton X-100 and Tween 20, which are nonionic surfactants. SDS was added in a concentration of 2%, and the others were each added in a concentration of 0.5%.

(2) Processing of Samples

Each (490 µL) of the above-mentioned various pretreatment solutions was added to each (10 µL) of the serum samples obtained from eight volunteers. The resultant mixture was diluted 5250-fold with ELISA buffer 2 without boiling. For comparison regarding effect, a control sample was prepared as follows: 50 mM Tris-HCl (pH 6.8, 2% SDS) (490 µL), serving as a pretreatment solution, was added to each (10 µL) of the above serums, stirred thoroughly, boiled, and diluted 5250-fold with ELISA buffer 2. A series of standard samples for calculating concentration were prepared as follows: The purified mAd which had been analyzed in Test Example 2 was added to 50 mM Tris-HCl (pH 6.8, 2% SDS), boiled, and serially diluted with ELISA buffer 2.

(3) Measurement of Total Adiponectin

An ELISA plate was sensitized with an anti-human adiponectin monoclonal antibody (64405) which had been diluted with PBS to 5 µg/mL, followed by blocking with ELISA buffer 2. A standard sample and a serum-treated solution (see above) were added to the plate, and reacted at room temperature for 1 hour. The plate was washed with ELISA wash solution. A biotin-labeled anti-human adiponectin monoclonal antibody (64404) which had been diluted 2,000-fold with ELISA buffer 2 was added for reaction at room temperature for 1 hour. HRP-avidin which had been diluted 2,000-fold with ELISA buffer 2 was added to the plate for reaction at room temperature for 30 minutes. The plate was washed with ELISA wash solution. For development of color, an OPD color-developing solution (250 mM citrate buffer containing 2 mg/ml orthophenylenediamine hydrochloride and 0.02% hydrogen peroxide, pH 5.0) was employed. The reaction was stopped by addition of a stopping solution (1.5N sulfuric acid, 1 mM EDTA-2Na), and absorbance at 492 nm was measured. Total adiponectin (concentration) levels of the serum samples which had been treated with respective pretreatment solutions were calculated with reference to the color values of developed color of the standard samples. A correlation analysis was performed, in which boiling with 50 mM Tris-HCl (pH 6.8, 2% SDS) represents the comparative condition (Table 5).

The analysis reveals that when samples were treated with an acid without addition of a surfactant, an excellent correlation coefficient was obtained, but the slope of the regression equation was 0.45, which is low as compared with a corresponding value obtained from the control. Under the coexistence of a surfactant, an improved correlation coefficient was obtained, and the measurements of the samples tended to approximate those of the control. In particular, remarkable effect was obtained from addition of an anionic surfactant. Thus, the pretreatment method of the present invention was found to achieve measurement of the total amount of adiponectin in a sample without boiling of the sample.

TABLE 5

|  | surfactant free | anionic 2% SDS | anionic 0.5% Neoperex F65 | cationic 0.5% Cortamine 24P | cationic 0.5% Cortamine 86P | nonionic 0.5% Triton X-100 | nonionic 0.5% Tween 20 |
| --- | --- | --- | --- | --- | --- | --- | --- |
| gradient | 0.45 | 0.88 | 0.83 | 0.58 | 0.57 | 0.6 | 0.59 |
| intercept | 0.9 | 0.3 | −0.6 | 0.4 | 0.2 | 0.1 | 0.2 |
| correlation coefficient ($r^2$=) | 0.966 | 0.994 | 0.996 | 0.984 | 0.993 | 0.992 | 0.986 |

(control): 50 mM Tris-HCl pH 6.8 (2% SDS), boiled

The invention claimed is:

1. A method for measuring a total amount of adiponectin present in a sample, comprising:
    adding an acid or a salt thereof to the sample to obtain a solution having a pH of 4 or less;
    allowing the acid or salt to react with the sample without boiling the combined sample and acid or salt; and
    subsequently performing an immunological assay of the sample for adiponectin;
    wherein the sample is an adiponectin multimer-containing sample.

2. The method of claim 1, wherein performing the immunological assay comprises employing an insoluble carrier on which an anti-adiponectin antibody is supported.

3. The method of claim 1, wherein a surfactant is added to the sample along with the acid or salt.

4. The method of claim 3, wherein the surfactant comprises an ionic surfactant.

5. The method of claim 3, wherein the surfactant comprises a nonionic surfactant.

6. The method of claim 3, wherein the surfactant comprises at least one alkyl sulfate.

7. The method of claim 3, wherein the surfactant comprises at least one alkylbenzene sulfonate.

8. The method of claim 3, wherein the surfactant is employed at a concentration of from 0.01 to 10%.

9. The method of claim 1, wherein the acid comprises an organic acid.

10. The method of claim 1, wherein the acid comprises an inorganic acid.

11. The method of claim 1, wherein the acid comprises at least one member selected from the group consisting of acetic acid, citric acid, hydrochloric acid, formic acid, tartaric acid and oxalic acid.

12. The method of claim 1, wherein allowing the acid or salt to react with the sample comprises allowing the acid or salt to react with the sample at a temperature of from 4 to 60° C. for a period of from 5 minutes to 24 hours.

13. The method of claim 1, wherein the immunoassay comprises an immunoassay selected from the group consisting of latex turbidimetric immunoassays, enzyme immunoassays, chemiluminescent enzyme immunoassays and radioimmunoassays.

14. The method of claim 2, wherein the insoluble carrier comprises polystyrene latex particles or a 96-well microplate made of styrene.

* * * * *